(12) United States Patent
Connelly et al.

(10) Patent No.: US 6,749,091 B2
(45) Date of Patent: Jun. 15, 2004

(54) UNIVERSAL REAGENT DISPENSER

(75) Inventors: Rowan T. Connelly, Fort Myers, FL (US); Alvin L. Waltman, Fort Myers, FL (US)

(73) Assignee: H. F. Scientific, Inc., Fort Myers, FL (US)

( * ) Notice: Subject to any disclaimer, the term of this patent is extended or adjusted under 35 U.S.C. 154(b) by 87 days.

(21) Appl. No.: 10/123,628

(22) Filed: Apr. 16, 2002

(65) Prior Publication Data

US 2003/0164386 A1 Sep. 4, 2003

Related U.S. Application Data

(60) Provisional application No. 60/283,965, filed on Apr. 16, 2001.

(51) Int. Cl.[7] ................................................. G01F 11/10
(52) U.S. Cl. ..................... 222/361; 222/336; 222/181.1; 285/148.23; 285/12
(58) Field of Search ................................. 222/361, 360, 222/363, 366, 181.1, 336, 368, 409, 453, 246, 243, 244, 561; 141/319, 378; 285/148.23, 12

(56) References Cited

U.S. PATENT DOCUMENTS

| | | | | |
|---|---|---|---|---|
| 1,904,756 A | * | 4/1933 | Wooster | 222/336 |
| 2,983,408 A | * | 5/1961 | Schwartz | 222/284 |
| 3,193,159 A | * | 7/1965 | Swindler | 222/336 |
| 4,266,813 A | * | 5/1981 | Oliver | 285/12 |
| 4,763,676 A | * | 8/1988 | Mizuno | 134/100.1 |
| 4,964,546 A | * | 10/1990 | Morrow et al. | 222/352 |
| 5,037,406 A | * | 8/1991 | Smith et al. | 604/301 |
| 5,259,537 A | * | 11/1993 | Beers et al. | 222/246 |
| 5,421,491 A | * | 6/1995 | Tuvim et al. | 222/336 |
| 5,513,777 A | * | 5/1996 | Yoda et al. | 222/325 |
| 5,573,281 A | * | 11/1996 | Keller | 285/40 |
| RE36,324 E | * | 10/1999 | Yoda et al. | 222/325 |
| 6,016,936 A | * | 1/2000 | Fan | 222/181.1 |

* cited by examiner

Primary Examiner—Gene Mancene
Assistant Examiner—Frederick C Nicolas
(74) Attorney, Agent, or Firm—William E. Noonan

(57) ABSTRACT

A single dosage dispenser for delivering chemical reagent to a test sample includes a body having an inlet and opposing outlet. The inlet is threadably and communicably engaged with a container holding a chemical reagent. The outlet includes a plurality of stepped receptacles for communicably receiving respective sizes of test sample holders. A spring actuated plunger is slidably mounted within the dispenser body between the inlet and the outlet. The plunger includes a reagent accommodating compartment. The spring urges the plunger into a first state wherein the plunger is communicably connected to the inlet for receiving a single dosage of reagent from the container. The user presses the plunger to drive the plunger within the dispenser body so that the compartment is communicably connected to the outlet. As a result, the reagent in the compartment is dispensed through the outlet into the test sample holder.

20 Claims, 9 Drawing Sheets

UNIVERSAL REAGENT DISPENSER

RELATED APPLICATION

This application claims the benefit of U.S. Provisional Patent Application Serial No. 60/283,965 filed Apr. 16, 2001.

FIELD OF THE INVENTION

This invention relates to a device for dispensing chemical reagents into water test samples so that such samples may be chemically analyzed.

BACKGROUND OF THE INVENTION

Chemical reagents are widely employed in the photometric testing of water for constituents such as chlorine. A number of devices are available for dispensing a single dosage of chemical reagent into the test sample. Typically, the dispensing device is first attached to a bottle containing the chemical reagent. The dispenser is then inverted and positioned over a test tube, cuvette or other receptacle containing the test sample. The mechanism is operated, normally by depressing a plunger, to dispense the chemical reagent into the test sample.

Known reagent dispensers exhibit a number of disadvantages. Although, cuvettes and other test sample holders come in a wide variety of shapes and sizes, most available dispensers are designed for use with only a single type of holder or, at most, a limited number of holders. It can also be difficult to accurately orient the dispenser over the holder so that dispensing is performed cleanly and efficiently. The lower dispensing end of the device is apt to accidentally dip into the test sample. This can contaminate the sample and foul or clog the dispenser.

Conventional reagent dispensers also employ a housing that is not optimally sealed. As a result, when the dispenser is operated, powder reagent residue tends to collect along the dispenser shaft and enter the housing. This also tends to foul the dispensing device and can cause the apparatus to malfunction.

One currently available reagent dispenser features an O-ring spring plunger operation. This mechanism does not feature an optimally positive, accurate and efficient dispensing operation.

SUMMARY OF THE INVENTION

It is therefore an object of the present invention to provide a hand held device for simply, accurately and efficiently dispensing a single dosage of chemical reagent into a test sample.

It is a further object of this invention to provide a dispenser that is quickly, conveniently and effectively interengagable with both a threaded bottle containing reagent and a holder that accommodates a test sample.

It is a further object of this invention to provide a universal reagent dispenser that is effective for use with virtually all sizes and shapes of test sample holders.

It is a further object of this invention to provide a chemical reagent dispenser that avoids contaminating the sample being tested.

It is a further object of this invention to provide a chemical reagent dispenser that resists fouling, clogging and malfunctioning.

It is a further object of this invention to provide a universal reagent dispenser that avoids accidental spilling of the chemical reagent.

It is a further object of this invention to provide a chemical reagent dispenser featuring an improved positive spring operation.

It is a further object of this invention to provide a chemical reagent dispenser that accurately, reliably and efficiently delivers a single dosage of a chemical substance to a cuvette, test tube or other container holding a test sample.

This invention features a single dosage, universal chemical reagent dispenser including a dispenser body having an inlet that is communicably interengagable with a supply of reagent and an axially offset outlet that is communicably interengagable with a test sample holder. There is a spring loaded reciprocating plunger mounted slidably within a cavity in the dispenser body between the inlet and the outlet. The plunger carries an actuator member externally of the dispenser body. A single dosage chemical accommodating compartment is formed through the plunger. A helical compression spring urges the plunger into a first position wherein the plunger compartment is communicably aligned with the inlet such that a single dosage of chemical reagent is delivered into the compartment. Depressing the plunger actuator member causes the plunger to slide through the dispenser body against the spring until the plunger compartment communicates with the offset outlet. As a result, the single dosage of chemical reagent is dispensed through the outlet into the test holder that is engaged with the outlet.

In a preferred embodiment, the inlet includes thread for operably interengaging corresponding threads carried by a bottle or other chemical reagent container. An annular seal may be disposed between the mouth of the reagent container and the inlet of the dispenser body. The outlet may include a plurality of concentric, stepped receptacles. Each receptacle respectively interengages one or more corresponding test sample holders. The dispenser body may include an upper passageway segment that is communicably connected between the inlet and the plunger compartment and an offset lower passageway segment that is communicably connected between the plunger compartment and the outlet.

The plunger may include a shaft-like plunger member that is longitudinally slidable through the channel in the dispenser body. The plunger shaft may include a proximal end that extends outwardly from the body and is attached to the actuator member. The actuator member may comprise a button or tab. The distal end of the shaft may include a recess that receives one end of the spring. The opposite end of the spring may interengage an inside wall of the dispenser body.

The plunger shaft may further include a circumferential groove that accommodates an annular seal. The seal prevents residual chemical reagent from migrating along the shaft between the seal and the actuator member. This reduces fouling between the shaft and the dispenser body and resultant malfunctioning of the device. The plunger shaft may also include an elongate longitudinal notch that is interengaged by a indexing element, set screw, detent or other element carried within the dispenser body. This limits movement of the plunger outwardly from the dispenser body and prevents unintended removal of the plunger from the body. It also orients the plunger properly within the channel such that the compartment is alignable with the inlet and the outlet when the plunger is in the first and second positions respectively.

A closure or cap may be attached to the dispenser. The closure is selectively interengagable with the outlet to close the outlet when the dispenser is not in use. The lower passageway may include a sharp edge opening to prevent buildup of channel reagent in the lower passageway.

DETAILED DESCRIPTION OF PREFERRED EMBODIMENTS

Other objects, features and advantages will occur from the following description of a preferred embodiment and the accompanying drawings, in which.

Figure 1:
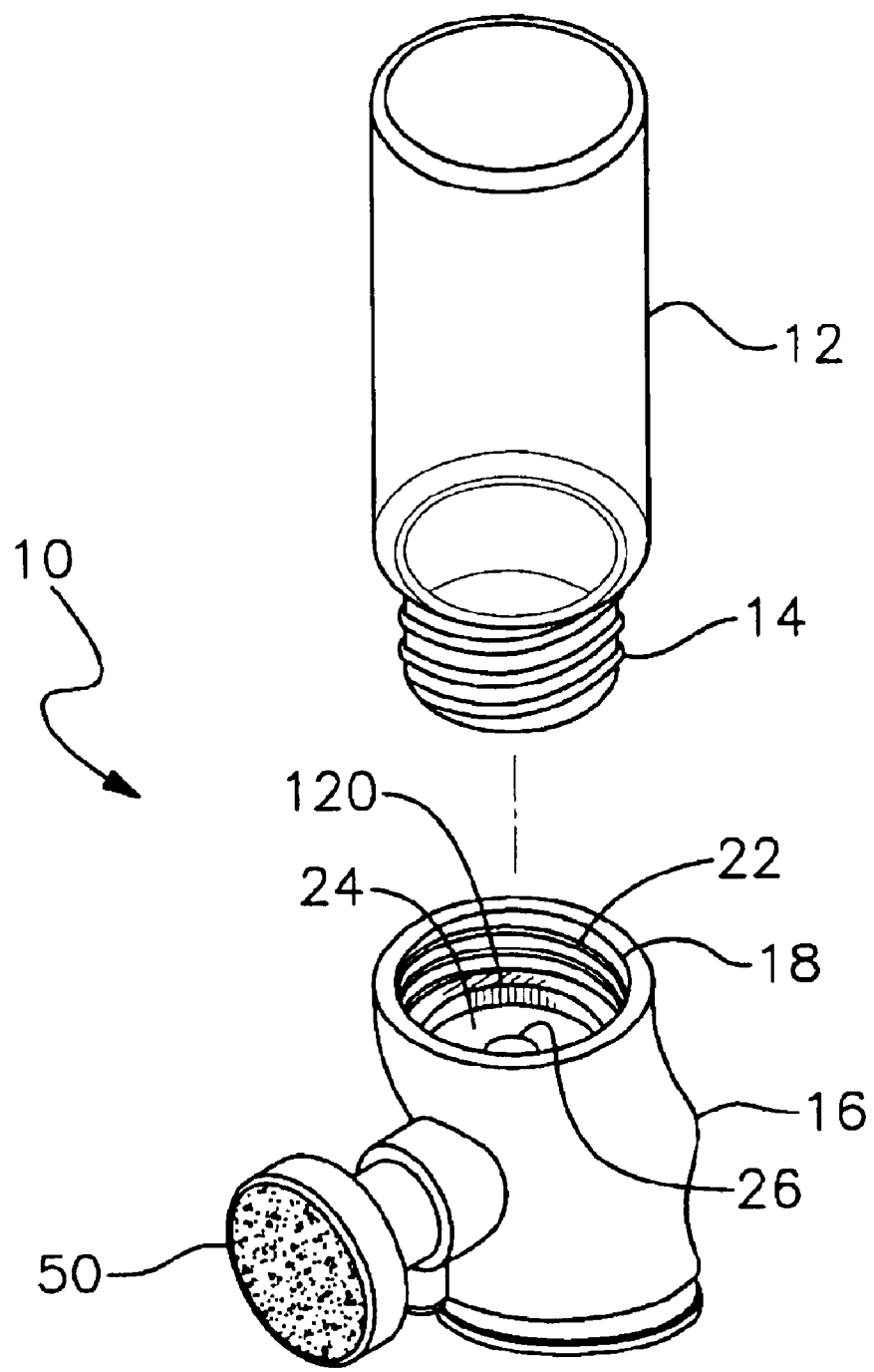
FIG. 1 is an isometric view of the universal chemical reagent dispensing device of this invention with a reagent container positioned above the inlet of the dispenser.
Figure 2:
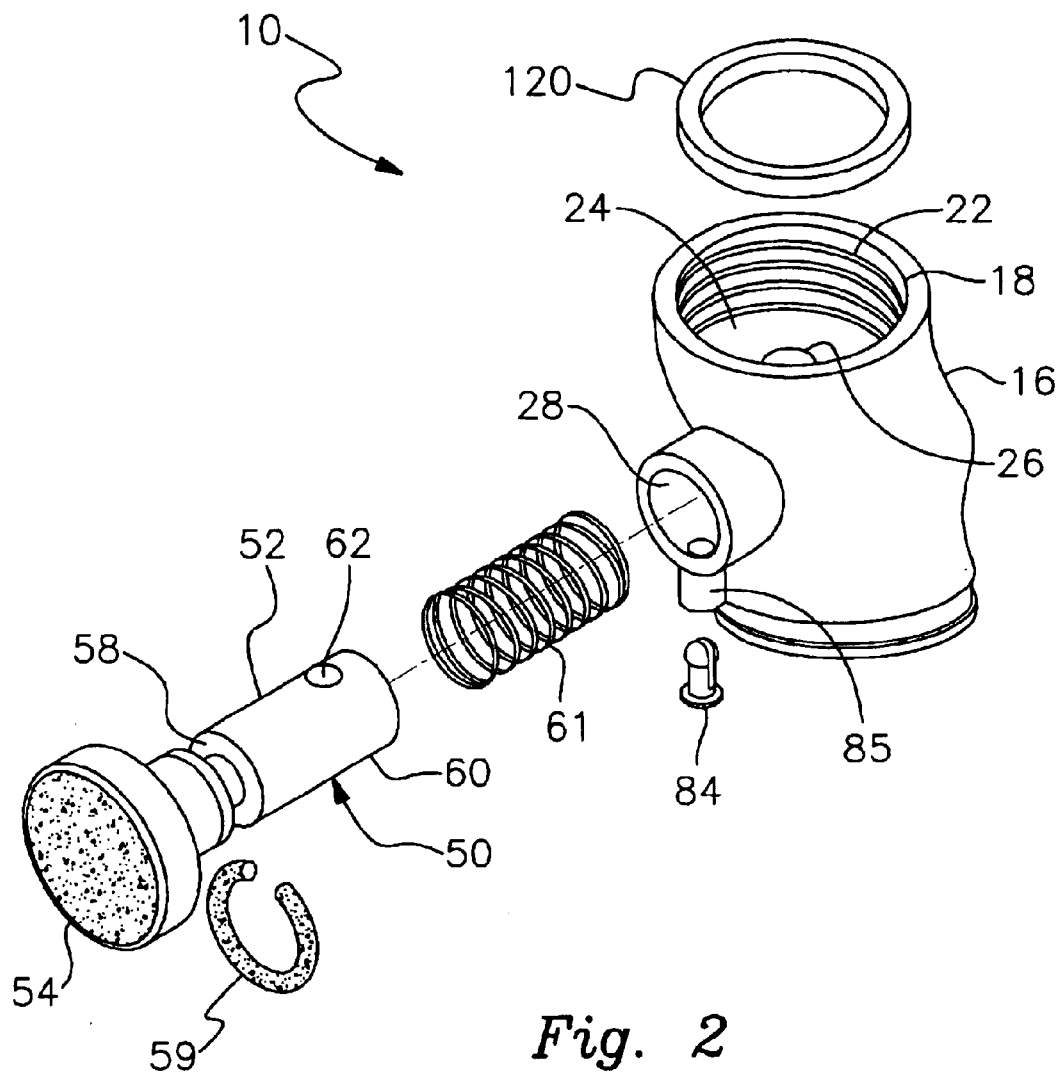
FIG. 2 is an exploded view of the dispenser.

There is shown in FIGS. 1 and 2 a universal chemical reagent dispensing device 10 that is designed for delivering a single dosage of a selected reagent into a cuvette so that a test sample within the cuvette may be photometrically tested in a known manner. The reagent (not shown in FIGS. 1 and 2) typically comprises a powdered substance that is accommodated in a transparent glass or plastic cuvette 12 (FIG. 1). The cuvette has a generally cylindrical shape and carries, at its lower end, a reduced diameter, threaded opening 14. The reagent accommodating cuvette is threadably interengaged with a dispenser body 16. The dispenser body, which is shown alone in FIG. 3, includes an interiorly threaded inlet 18 formed at its upper end. Interior threads 22 are sized to operably interengage the exterior threads on reduced diameter portion 14 such that a cuvette 12 is threadably interengaged with inlet 18. Body 16 also features a floor 24, FIGS. 1–3, which is formed at the inner end of inlet 18. An upper passageway 26, which typically comprises a countersunk hole (see FIG. 3), is formed through floor 24. Passageway 26 communicates with a plunger channel 28 (FIGS. 2 and 3) that is formed transversely through dispenser body 16. A second, lower passageway portion 30 also communicates with channel 28 but is linearly offset from upper passageway 26. Once again, passageway portion 30 comprises a countersunk hole.

Figure 3:
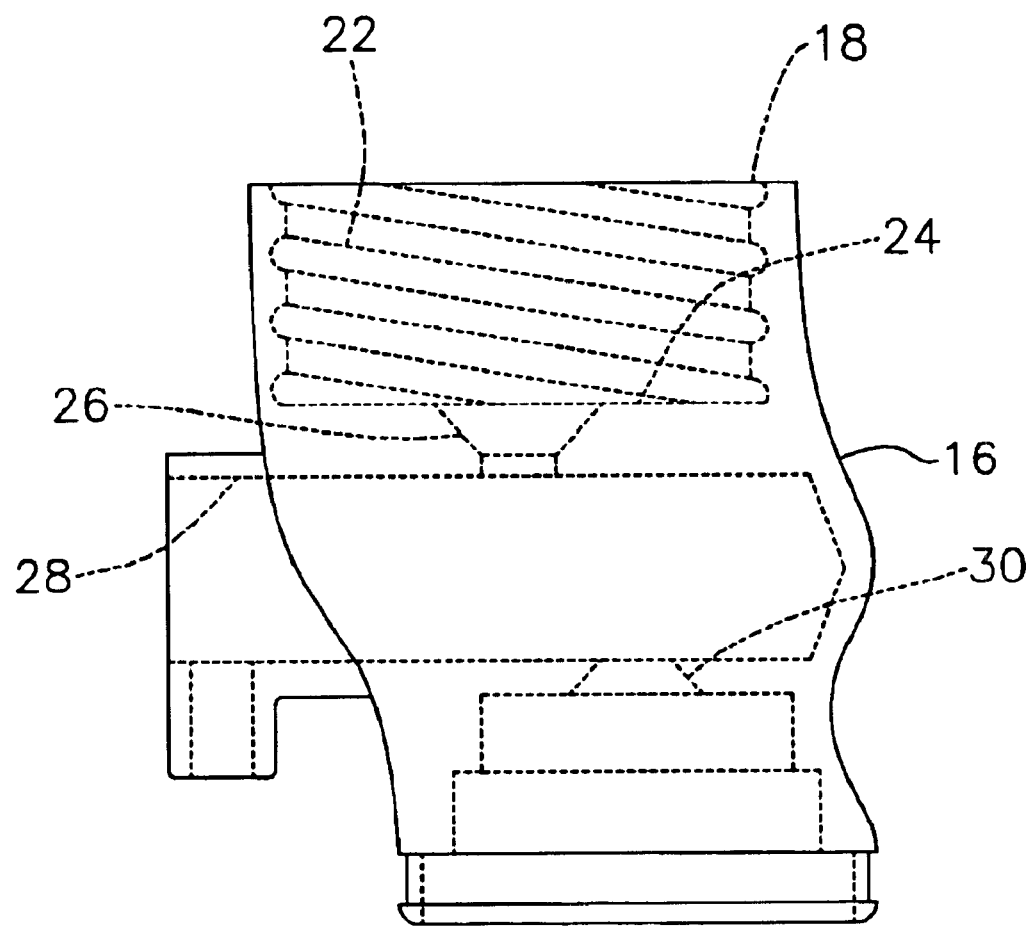
FIG. 3 is an elevational, side view of the dispenser body.
Figure 4:
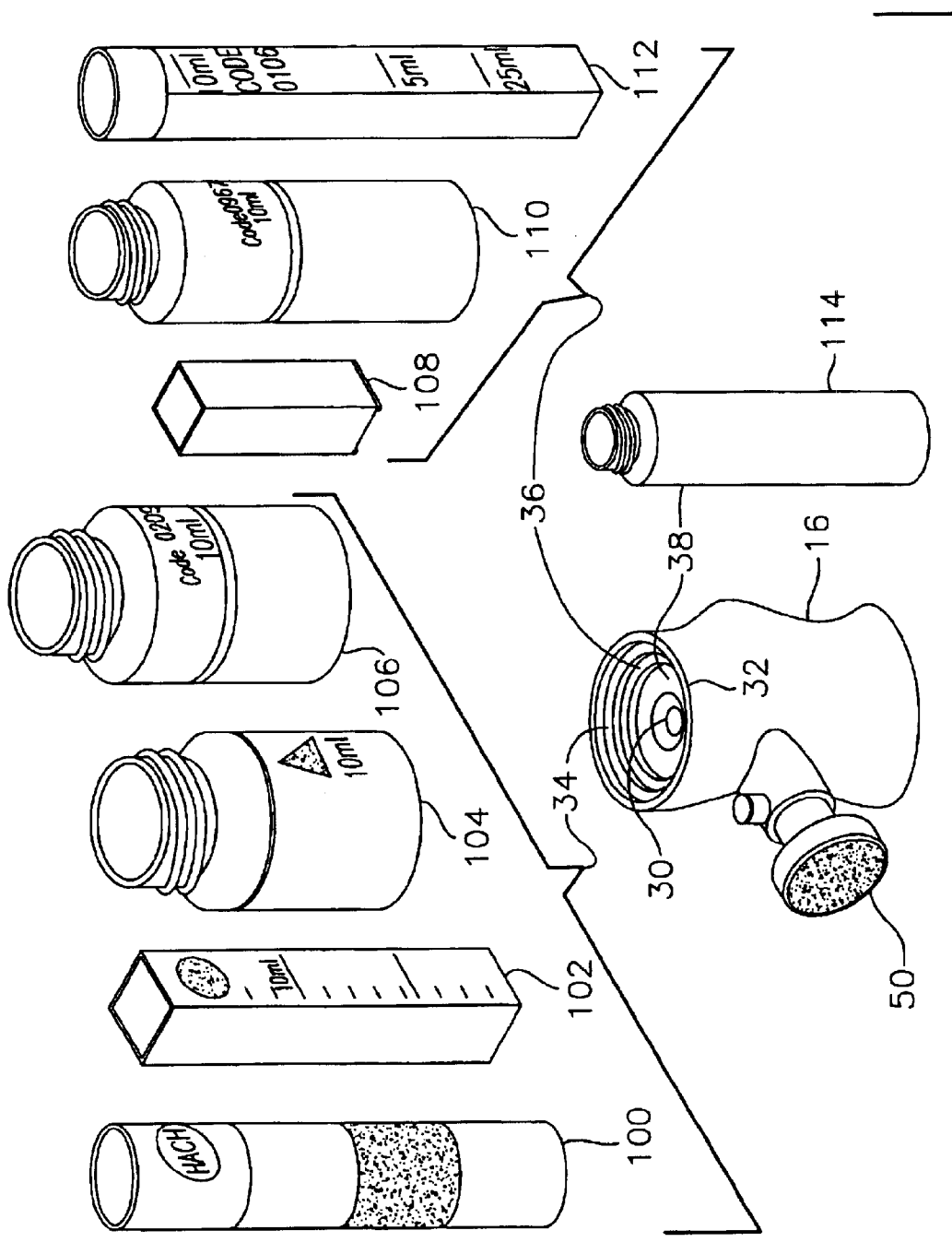
FIG. 4 is an isometric view of the bottom (outlet) end of the dispenser and various test sample holders that are operably interengagable with respective stepped receptacles of the outlet.

As best shown in FIGS. 3–4, the bottom of dispenser body 16 includes a generally cylindrical outlet 32 that surrounds and communicates with lower passageway portion 30. Outlet 32 includes a plurality of stepped receptacles 34, 36 and 38, which respectively increase in depth and decrease in diameter. These receptacles are designed for communicably engaging a test sample holder in the manner described more fully below. A cap or closure may be selectively engaged with outlet 32 in a manner described below.

As shown in FIG. 4, outlet 32 is designed to snugly receive and engage a wide variety of conventionally available test sample holders (e.g. cuvettes) such that the outlet communicates with the holder. In particular, wide diameter receptacle 34 receives and mates with each of the holders 100, 102, 104 and 106. In each case, the outer side wall of receptacle 34 more or less snugly surrounds the opening of the cuvette and the opening itself engages the annular step of the receptacle. Likewise, intermediate receptacle 36 receives and is communicably interengaged with cuvette holders 108, 110 and 112. The inner recess or receptacle 38 similarly accommodates the mouth of holder 114. The mouth or opening of each cuvette engages a respective receptacle so that the cuvette is communicably engaged with lower passageway portion 30. Likewise, in each instance, the receptacle of the outlet surrounds and receives the mouth of the cuvette; no portion of the dispenser or its outlet 32 is inserted into the cuvette or test holder. Accordingly, the liquid being tested is not contaminated by the dispenser and the outlet is not clogged.

Figure 5:
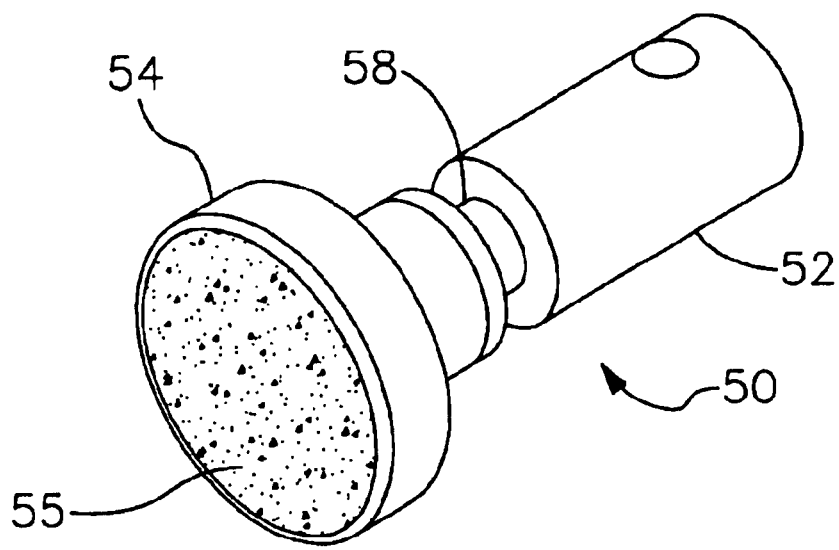
FIG. 5 is an isometric view of the plunger.
Figure 6:
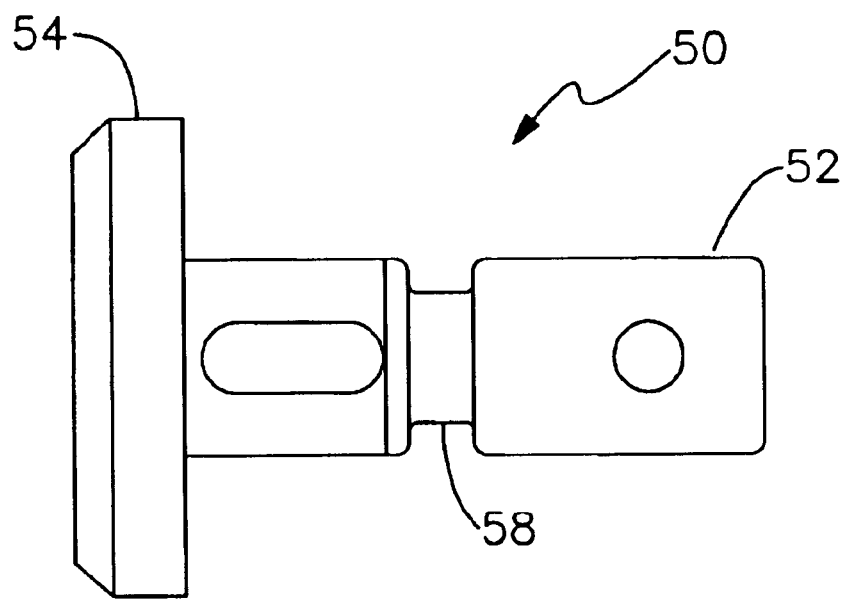
FIG. 6 is an elevational, bottom view of the plunger.

A plunger 50 is operably engaged with dispenser body 16 in the manner depicted in FIGS. 1, 2 and 4. More specifically, the plunger is slidably received in transverse channel 28. As illustrated in FIG. 2 and as shown alone in FIGS. 5 and 6, plunger 50 includes a generally cylindrical rod or shaft 52. An outer end of the rod carries an actuator member or button 54 having a textured engagement surface 55. An optional recess, not shown, may be formed at the opposite, inner end of rod 52. An annular groove 58 is formed approximately midway between the inner and outer ends. A complementary annular or semi-annular O-ring wiper 59, which may be composed of felt cord or similar material, is received (FIGS. 2 and 7) within annular groove 58. This O-ring effectively forms a seal that restricts residual reagent from migrating outwardly along the outer surface of rod 52 and which would otherwise clog and interfere with operation of the plunger. O-ring 59 also wipes residual reagent from the wall of channel 28 during operation of the plunger so that clogging is further reduced. An inner segment 60 of rod 52 includes a transverse hole or compartment 62 that is formed diametrically through the rod. A second, outer segment 64 of the rod includes a longitudinal slot 66. The function of these components is described more fully below.

It should be noted that dispenser body 16 and plunger 50 may be composed of various plastics, metals and metal alloys. A rugged and durable plastic such as white acetyl or Delrin (™) is especially preferred because such material provides a relatively long operational life. It should be noted that the materials composing dispenser 10 may be varied within the scope of this invention.

Figure 7:
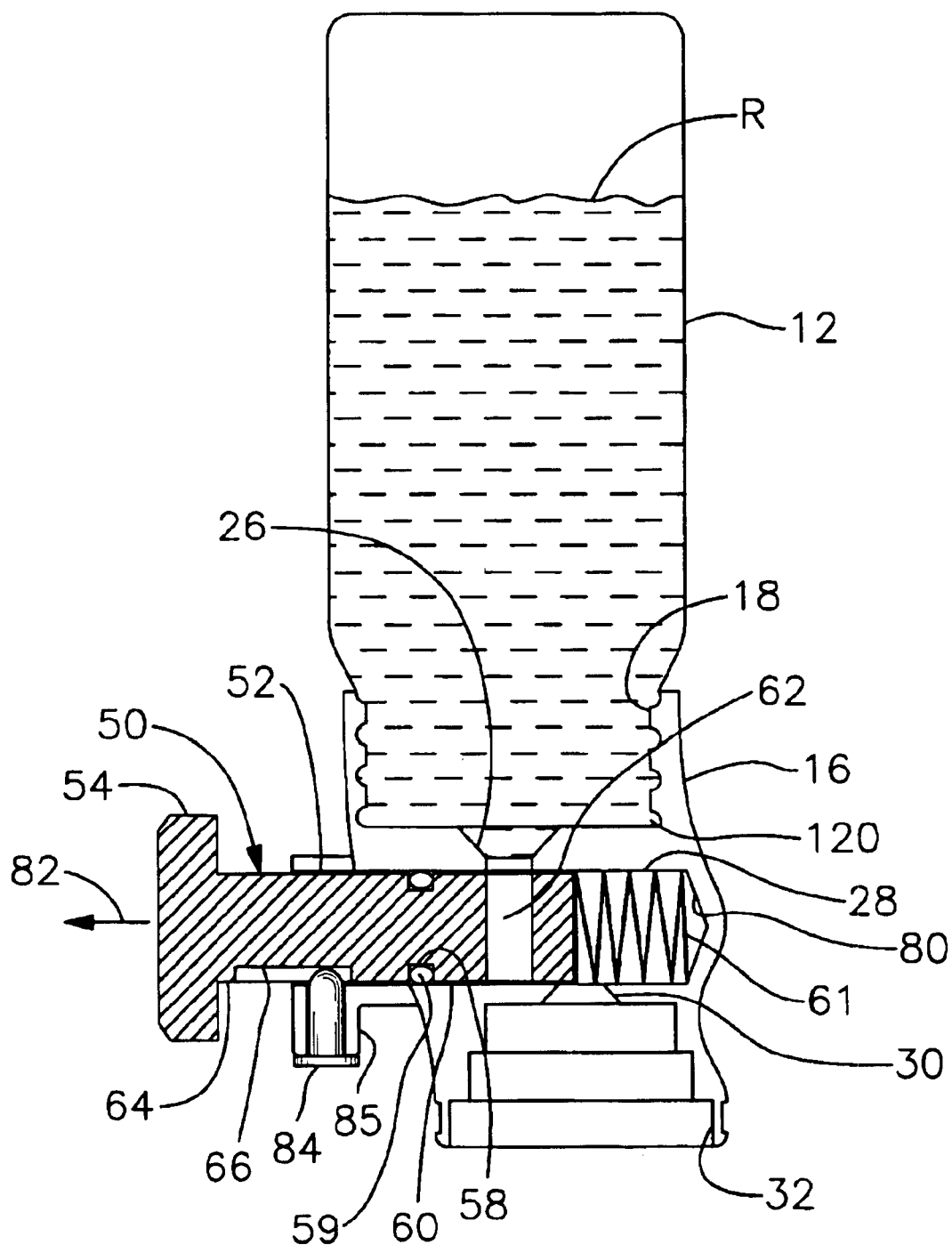
FIG. 7 is an elevational cross sectional view of the dispenser with the plunger in a first, closed state.

Plunger 50 is operably mounted in dispenser body 16 in the manner shown in FIG. 7. The plunger is received by and slidable within transverse channel 28. A helical compression spring 61 (see also FIG. 2) is also disposed within channel 28. Spring 61 extends between the distal end of plunger rod 52, and a converging inner wall 80 of dispenser body 16. Spring 61 is biased to urge plunger 50 outwardly relative to body 16 as indicated by arrow 82. An indexing pin 84 is inserted through a receptacle 85 formed in the bottom of body 16 and is received in longitudinal slot 66 in rod 52. The indexing pin prevents the plunger from being inadvertently removed from cavity 28. The pin also correctly orients the plunger with channel 28 during assembly so that compartment 62 is selectively alignable with passageways 26 and 30. When plunger 50 is in the fully extended state shown in FIG. 7, the compartment 62 formed transversely through rod 52 is generally aligned with upper passageway portion 26 of dispenser body 16. At the same time, compartment 62 is offset from and not axially aligned with lower passageway 30. Compartment 62 has a size that accommodates a single dosage of chemical reagent.

Figure 8:
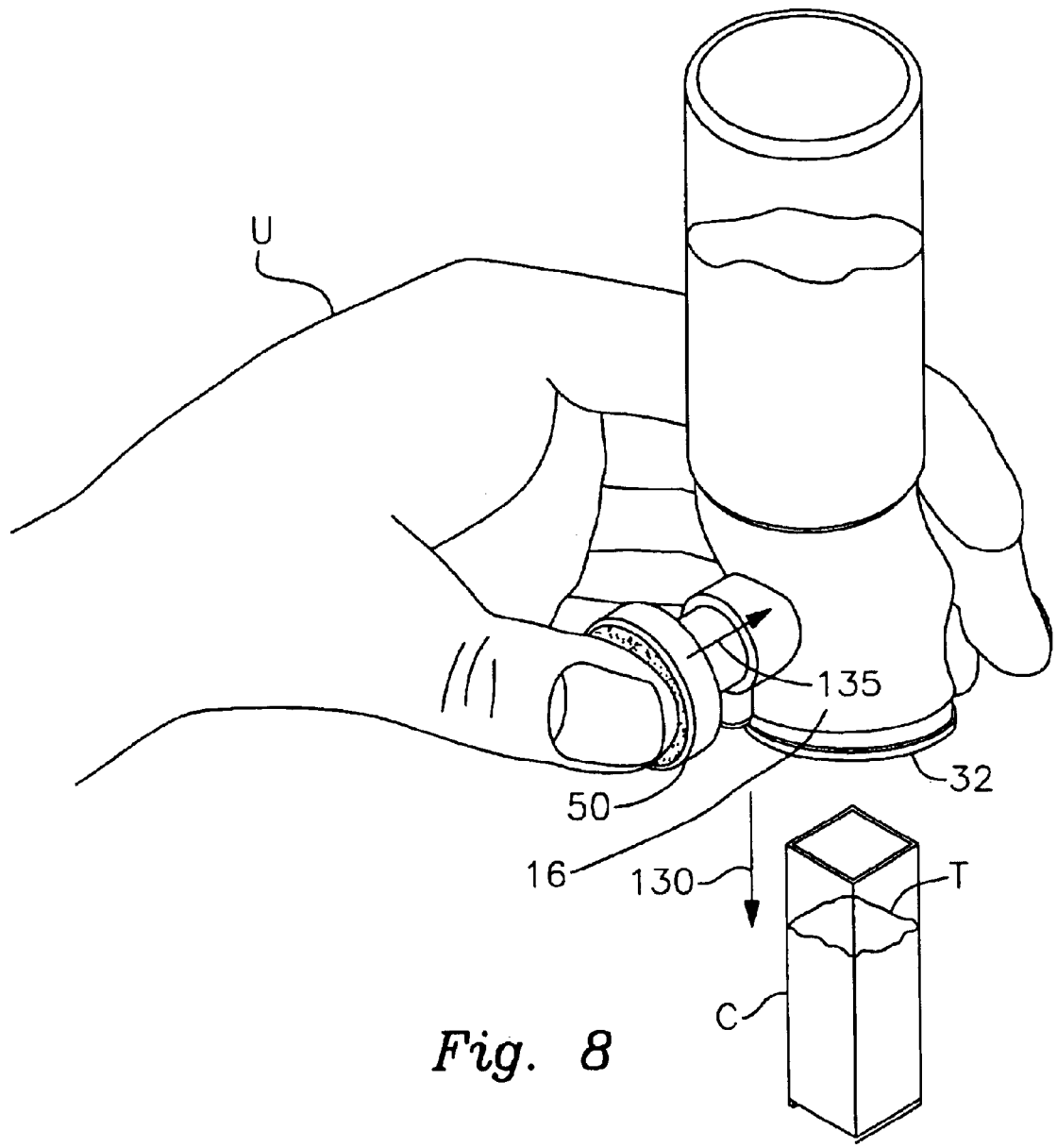
FIG. 8 is an isometric view of the dispensing device with the plunger being operated to dispense chemical reagent into a test sample holder.

To operate the dispenser, a bottle, vial, cuvette or other container 12 containing an appropriate chemical reagent R (FIG. 7) is threadably interengaged with inlet 18 of dispenser body 16. As shown in FIGS. 1 and 2, an annular silicone sealing washer 120 may be employed within inlet 18 to form a tight sealing fit between the container 12 and the dispenser body 16. Initially, dispenser 10 is inverted and inlet 18 is screwed onto threaded opening 14 of upright container 12. Washer 120 effectively seals the assembly so that reagent is not spilled when the dispenser body 16 is returned to the upright condition and container 12 is inverted as depicted in FIG. 7. As shown in FIG. 8, user U grasps body 16 with container 12 attached and positions outlet 32 over a cuvette C containing a test sample T. Because outlet 32 has several differently sized receptacles, it effectively forms a "universal" fitting that is operably engagable with virtually all makes and models of cuvettes and other types of test sample holders. The user lowers dispenser 10 in the direction of arrow 130 until outlet 32 matingly and communicably engages cuvette C. (See FIG. 9) The open upper end 133 of the cuvette is thereby received and surrounded by wide diameter receptacle 34. In other embodiments, different types and sizes of cuvettes may be received within stepped receptacles 36 and 38. In either case, the receptacle completely surrounds the cuvette but no portion of dispenser 10 is inserted into the cuvette or touches the test sample.

Initially spring 61 urges plunger 50 outwardly from body 16 in the direction of arrow 82. Upper passageway portion 26 and transverse plunger compartment 62 are thereby communicably aligned. Accordingly, as shown in FIG. 7, reagent R in container 12 is transmitted (drops) through upper passageway portion 26 into compartment 62. As previously indicated, the amount of reagent deposited within the compartment generally represents a single dosage of the chemical reagent. The lower end of the compartment is offset from passageway 30 and outlet 32. As a result, the dispenser is effectively closed and no reagent is dispensed into cuvette C.

Figure 9:
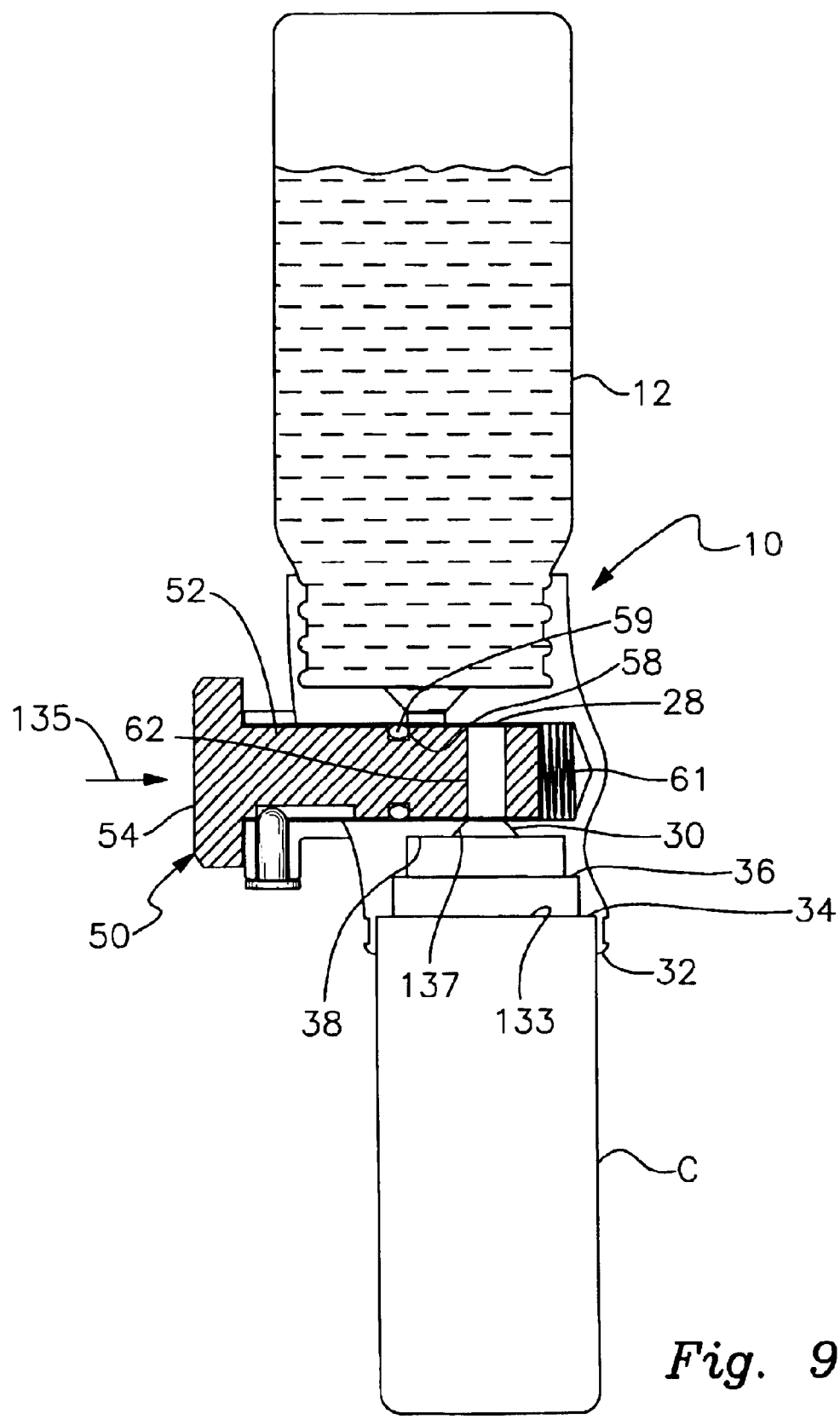
FIG. 9 is an elevational, cross sectional view similar to FIG. 7 of the dispensing device with the plunger in the second, open state wherein the reagent is dispensed into a test sample holder.

The user U (FIG. 8) next operates the dispenser by depressing plunger 50, in the manner shown in FIGS. 8 and 9. The user presses his or her thumb against button 54, as indicated by arrow 135, and pushes the plunger slidably through channel 28 until the button engages body 16. At this point, plunger 50 reaches its inner limit of travel. Spring 61 is fully compressed. Transverse plunger compartment 62 is moved with plunger 50 forwardly through channel 28. At the inner limit of the plunger's travel, compartment 62 is communicably aligned with lower passageway portion 30. As a result, the dispenser is open. Gravity causes the single dosage of reagent within compartment 62 to drop out of the compartment and through lower passageway portion 30 into outlet 32. From there, the reagent is dispensed into the communicably engaged cuvette C. Passageway 30 is preferably chamfered inwardly from bottom to top so that the passageway includes a sharp edge opening 137 adjacent aligned compartment 62. This prevent residual reagent from building up in the lower passageway. As a result, the proper dosage of reagent is fully dispensed and potential spills are avoided.

After the reagent is dispensed into the cuvette, the user releases plunger 50. Spring 61 resumes its initial condition and pushes plunger 50 outwardly so that it returns to its closed state shown in FIG. 10. Subsequent doses may then be dispensed in an analogous manner to successive cuvettes.

The dispensing device of this invention is fast and easy to operate and exceptionally reliable. Residue does not collect along the plunger rod or within other internal operating parts of the dispenser. Accordingly, a reliable operation is provided over thousands of uses. The universal dispenser is particularly convenient because it can be used with virtually all types of cuvettes and other test sample holders. By engaging the holder with the outlet and pressing the plunger, chemical reagent is delivered reliably, accurately and completely without spilling or contaminating the sample and without clogging the dispenser.

Figure 10:
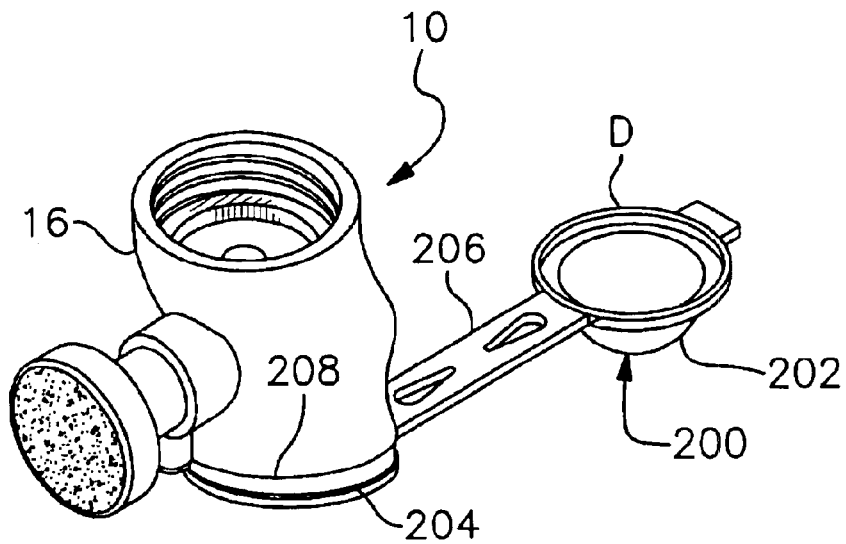
FIG. 10 is an upper perspective view of the reagent dispenser as further equipped with a releasable closure.
Figure 11:
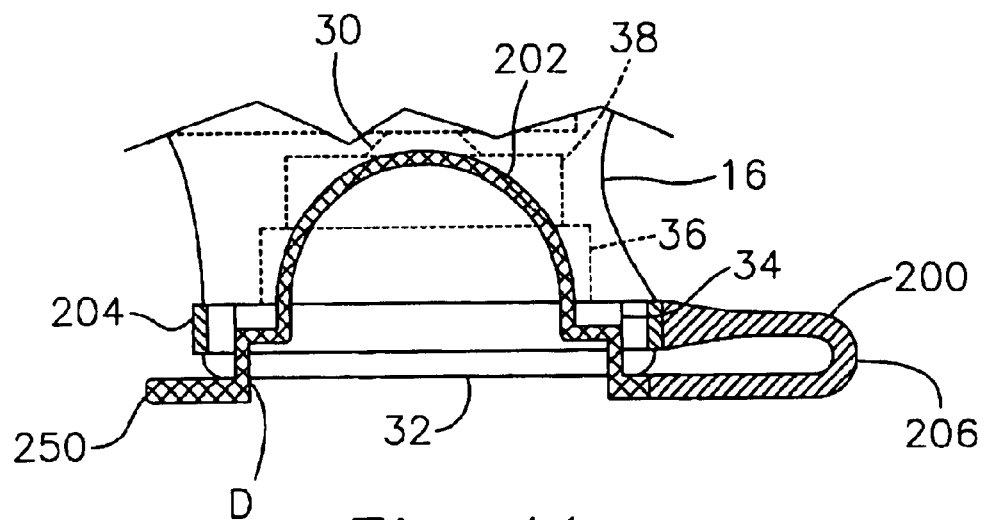
FIG. 11 is an elevational, fragmentary and partly cross sectional view of the lower end of the dispensing device with the closure engaged with the outlet.

As shown in FIGS. 10 and 11, reagent dispenser 10 may be equipped with an optional closure device 200. The closure comprises a rounded plastic cap 202 that is connected unitarily to a retaining ring 204 by an elongate strap 206. Closure 200 is preferably composed of a molded plastic such as white polyethylene. Retaining ring 204 is snuggly snap fitted into an annular groove 208 formed about dispenser body 16 proximate the lower outlet.

As best shown in FIG. 11, cap 202 is selectively engaged with outlet 32 of dispenser body 16 such that the outlet is effectively sealed in a closed condition. The cap comprises a flexible plastic and has a circumferential shoulder 240 with a diameter that is slightly larger than the diameter of the widest outlet receptacle 34. The cap should also press easily into the outlet opening. As shown in FIG. 11, cap 202 has a rounded cross sectional shape that does not interfere with the reduced diameter stepped receptacles 36 and 38.

To seal the dispenser outlet closed, the user simply grasps cap 202, bends strap 206 and presses the cap into engagement with outlet 32 in the manner shown in FIG. 11. Circumferential shoulder 240 interengages the side wall of stepped receptacle 34 to hold the cap in place such that an airtight seal is formed against the widest stepped receptacle. This prevents accidental spillage of reagent from the dispenser when the dispenser is not in use. Moreover, moisture is restricted from entering the dispenser and fouling the reagent. The cap is removed from the outlet when needed by simply grasping the outer lip 250 and pulling the flexible plastic closure away from the outlet.

From the foregoing it may be seen that the apparatus of this invention provides for dispensing chemical reagents into water test samples so that such samples may be chemically analyzed. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

Other embodiments will occur to those skilled in the art and are within the following claims:

What is claimed is:

1. A single dosage, universal chemical reagent dispenser comprising:
   a dispenser body having an inlet for communicably interengaging a supply of reagent and a communicably offset outlet for communicably interengaging a test sample holder;

a plunger mounted slidably for reciprocating movement through a channel in said dispenser body, said plunger having a single dosage chemical reagent accommodating compartment formed therein, said channel being in communication with said inlet and said outlet, said plunger carrying an actuator externally of said dispenser body, said actuator being depressed to slide said plunger through said channel, said plunger including an elongate shaft that is slidable in said channel; and a resilient mechanism for urging said plunger into a first position in said channel wherein said plunger compartment communicates with said inlet such that a single dosage of chemical reagent is deliverable through said inlet to said compartment, said mechanism permitting said plunger to be slid selectively into a second position in said channel wherein said plunger compartment communicates with said outlet such that the single dosage of chemical reagent in said compartment is dispensed through said outlet into the interengaged test sample holder;

said shaft including a circumferential groove that accommodates an annual seal, said seal being disposed between said plunger and an inner wall of said channel for restricting chemical reagent from migrating along said shaft externally of said dispenser body.

2. The device of claim 1 in which said inlet includes threads for interengaging corresponding threads carried by a container holding the supply of reagent.

3. The device of claim 2 further including an annular seal for interengaging said inlet and a mouth of the reagent container.

4. The device of claim 1 in which said outlet includes a plurality of substantially concentric, stepped receptacles, each receptacle for respectively interengaging at least one corresponding test sample holder.

5. The device of claim 1 in which said dispenser body includes an upper passageway segment communicably interconnecting said inlet and said plunger compartment.

6. The device of claim 5 in which said dispenser body includes a lower passageway segment linearly offset from said upper passageway segment and communicably interconnecting said plunger compartment and said outlet.

7. The device of claim 1 in which said shaft includes a proximal end that extends outwardly from said body and to which said actuator is attached.

8. The device of claim 7 in which said actuator includes a button.

9. The device of claim 7 in which said shaft includes a distal end that interengages said resilient mechanism.

10. The device of claim 1 in which said resilient mechanism includes a helical compression spring.

11. The device of claim 1 in which said shaft includes a longitudinal notch interengaged by an indexing element attached to said dispenser body for orienting said plunger within said channel such that said compartment is alignable with said inlet and said outlet when said plunger is in said first and second positions respectively.

12. The device of claim 1 further including a closure attached to said dispenser body and being selectively interengagable with said outlet to close said outlet when said dispenser is not in use.

13. The device of claim 6 in which said lower passageway segment includes a sharp edge opening to prevent buildup of chemical reagent in said lower passageway segment.

14. A single dosage, universal chemical reagent dispenser comprising:

a dispenser body having an inlet for communicably interengaging a supply of reagent and a communicably offset outlet for communicably interengaging a test sample holder;

a plunger mounted slidably for reciprocating movement through a channel in said dispenser body, said plunger having a single dosage chemical reagent accommodating compartment formed therein, said channel being in communication with said inlet and said outlet, said plunger carrying an actuator externally of said dispenser body, said actuator being depressed to slide said plunger through said channel, said plunger including an elongate shaft that is slidable in said channel; and a resilient mechanism for urging said plunger into a first position in said channel wherein said plunger compartment communicates with said inlet such that a single dosage of chemical reagent is deliverable through said inlet to said compartment, said mechanism permitting said plunger to be slid selectively into a second position in said channel wherein said plunger compartment communicates with said outlet such that the single dosage of chemical reagent in said compartment is dispensed through said outlet into the interengaged test sample holder;

said shaft including a longitudinal notch interengaged by an indexing element attached to said dispenser body for orienting said plunger within said channel such that said compartment is alignable with said inlet and said outlet when said plunger is in said first and second positions, respectively.

15. The device of claim 14 in which said outlet includes a plurality of substantially concentric, stepped receptacles, each receptacle for respectively interengaging at least one corresponding test sample holder.

16. A single dosage, universal chemical reagent dispenser comprising:

a dispenser body having an inlet for communicably interengaging a supply of reagent and a communicably offset outlet for communicably interengaging a test sample holder;

a plunger mounted slidably for reciprocating movement through a channel in said dispenser body, said plunger having a single dosage chemical reagent accommodating compartment formed, said channel being in communication with said inlet and said outlet, said dispenser body including an upper passageway communicably interconnecting said inlet and said compartment and a lower passageway segment linearly offset from said upper passageway segment and communicably interconnecting said compartment and said outlet;

a resilient mechanism for urging said plunger into a first position in said channel wherein said plunger compartment communicates with said inlet such that a single dosage of chemical reagent is deliverable through said inlet to said compartment, said mechanism permitting said plunger to be slid selectively into a second position in said channel wherein said plunger compartment communicates with said outlet such that the single dosage of chemical reagent in said compartment is dispensed through said outlet into the interengaged test sample holder;

said lower passageway segment including a sharp edge opening to prevent buildup of chemical reagent in said lower passageway segment.

17. The device of claim 16 in which said plunger carries an actuator externally of said dispenser body, said actuator being depressed to slide said plunger through said channel.

18. The device of claim 17 in which said plunger includes an elongate shaft that is longitudinally slidable in said channel.

19. The device of claim 18 in which said shaft includes a circumferential groove that accommodates an annular seal, said seal being disposed between said plunger and an inner wall of said channel for restricting chemical reagent from migrating along said shaft externally of said dispenser body.

20. The device of claim 16 in which said outlet includes a plurality of substantially concentric, stepped receptacles, each receptacle for respectively interengaging at least one corresponding test sample holder.

* * * * *